(12) United States Patent  
Hogan

(10) Patent No.: US 8,870,376 B2  
(45) Date of Patent: Oct. 28, 2014

(54) NON-INVASIVE OPTICAL MONITORING

(71) Applicant: Joshua Noel Hogan, Los Altos, CA (US)

(72) Inventor: Joshua Noel Hogan, Los Altos, CA (US)

( * ) Notice: Subject to any disclaimer, the term of this patent is extended or adjusted under 35 U.S.C. 154(b) by 174 days.

(21) Appl. No.: 13/668,258

(22) Filed: Nov. 3, 2012

(65) Prior Publication Data

US 2014/0002793 A1 Jan. 2, 2014

Related U.S. Application Data

(60) Provisional application No. 61/628,709, filed on Nov. 4, 2011, provisional application No. 61/667,417, filed on Jul. 3, 2012.

(51) Int. Cl.
*A61B 3/14* (2006.01)
*A61B 3/10* (2006.01)
*A61B 3/00* (2006.01)

(52) U.S. Cl.
CPC .. *A61B 3/102* (2013.01); *A61B 3/14* (2013.01)
USPC ............ 351/206; 351/208; 351/221; 351/246

(58) Field of Classification Search
USPC .................................. 351/206, 208, 221, 246
See application file for complete search history.

*Primary Examiner* — Jack Dinh

(57) ABSTRACT

The invention provides a method and system for non-invasive analysis. In particular the inventive system relates optical techniques involving infra-red, visible or ultra violet radiation for imaging and analyzing surface and sub-surface structure of tissue and components of the eye. Embodiments of the invention further include Optical Coherence Tomography (OCT) techniques for sub-surface imaging and analysis, and incorporate instruments such as ophthalmoscopes, fundus cameras, for non-invasive imaging and analysis.

17 Claims, 5 Drawing Sheets ically set forth herein. This application is further is related to U.S. Pat. Nos. 7,526,329 and 7,751,862, the contents of both of which are incorporated by reference herein as if fully set forth herein. It is also related to U.S. patent application Ser. No. 12,924,316 titled Compact Isolated Analysis System with filing date Sep. 24, 2010 the contents of which is also incorporated by reference herein as if fully set forth herein.

NON-INVASIVE OPTICAL MONITORING

CROSS REFERENCES TO RELATED PATENTS OR APPLICATIONS

This application claims priority from U.S. provisional patent application 61/628,729, and priority from U.S. provisional application 61/61/667,417, the contents of both of which are incorporated by reference as if fully set forth herein. This application is further is related to U.S. Pat. Nos. 7,526,329 and 7,751,862, the contents of both of which are incorporated by reference herein as if fully set forth herein. It is also related to U.S. patent application Ser. No. 12,924,316 titled Compact Isolated Analysis System with filing date Sep. 24, 2010 the contents of which is also incorporated by reference herein as if fully set forth herein.

GOVERNMENT FUNDING

None.

FIELD OF THE INVENTION

The invention relates to in-vivo non-invasive imaging and analysis. In particular it relates to optical techniques involving both infra-red and shorter wavelength (visible or ultra violet) radiation for imaging and analyzing surface and sub-surface structure of tissue.

BACKGROUND

Ophthalmoscopes and Fundus cameras are commonly used to image the retina of the eye. Such devices typically use visible light to illuminate the retina. The use of visible light causes the pupil of the eye to substantially close which requires the user to view along the central axis of the eye and precludes off axis viewing. This limits the field of view of the retina and complicates the use of augmenting imaging systems, such as OCT systems. The use of infra-red light precludes direct viewing of the retina by a physician. Moreover, light in the visible wavelength is valuable in generating a detailed view of the retina. So, overcoming the tradeoff between the detail of visible light and the limitation imposed by pupil contraction needs to be solved for non-invasive in vivo analysis to be more useful in rapidly and efficiently monitoring targets such as the eye.

What is needed is a means of non-invasively analyzing in vivo targets and obtaining the best possible image of the region of interest in the target. In particular, what is needed for targets such as the eye, is a means to use visible light without having the target area obscured by the contraction of the pupil. Further needed is an improved means to use a combination of interferometrically acquired depth information and images obtained with radiant energy of visible light wavelengths to obtain measurements of eye components, such as the axial length of the eye, as well as the thickness of the retina, and measurements of three dimensional structures. Moreover, using depth information in conjunction with acquired images to align, combine, and overlap images of critical areas, such as the fovea, is also needed.

SUMMARY OF THE INVENTION

The invention provides a method and system that meets at least all of the above-recited needs. The invention taught herein is provides a means of non-invasive analysis of in-vivo tissue, and most particularly the eye. In particular the inventive system relates optical techniques involving infra-red, visible or ultra violet radiation for imaging and analyzing surface and sub-surface structure of tissue and components of the eye. Embodiments of the invention further include Optical Coherence Tomography (OCT) techniques for sub-surface imaging and analysis, and incorporate instruments such as ophthalmoscopes, fundus cameras, for non-invasive imaging and analysis.

In a preferred embodiment, the inventive method of analyzing a target includes the steps of intermittently illuminating the target with first radiation at at least one first wavelength; synchronously capturing at least some of the first radiation with a first camera to form a first image; storing the first image in memory; displaying the first image on at least one viewing device; observing the displayed first image manipulating the relative position of the first camera with respect to the target to observe a region of interest in the target, and storing at least one of the displayed images.

In another embodiment, the step of intermittently illuminating the target with the first radiation is interleaved with the further step of illuminating the target with at least one short burst of a second radiation at a second wavelength; and synchronously capturing at least a portion of the second radiation with a second camera to form a second image; storing the second image in memory; and combining the second image with the first image.

A system according to the invention comprises an illumination module operable to intermittently illuminate the target with first radiation at at least one first wavelength; a first camera operable to synchronously capture at least some of the first radiation to form a first image, a memory operable to store the first image; a display operable to display the first image on at least one viewing device; a control module operable to manipulate the relative position of the first camera with respect to the target to observe a region of interest in the target; an OCT system operable to perform at least one interferometric based depth scan by means of an interferometric device at a first location of at least one component of the target, wherein the location of the depth scan is registered with the first image obtained by the first camera.

Alternatively, the inventive system includes a second camera wherein the illuminating module intermittently illuminates the target with a first radiation, and in an interleaved manner, illuminates the target said with at least one short burst of a second radiation at a second wavelength; synchronously capturing at least a portion of the second radiation with at second camera to form a second image; and storing said second image in memory. The first and second image can be combined in various ways, by subtraction of elements, adding of elements, or overlapping the first and second image.

It can be appreciated that when the target is an eye, the invention provides a means to produce images of the fovea of the retina. Moreover, in embodiments of the system including an interferometric device, such as, for example, an OCT system, the interferometric depth scan is registerable with the image obtained by a camera. Thus, when the target is and eye, for example, the inventive system provides a measurement of the axial length of the eye. Moreover, the system can measure tissue thickness of eye components, such as the thickness of the retina, or components of the anterior chamber. Selection of short bursts of radiation permit capture of images faster than the pupil can contract, thereby maximizing the amount of the target that can be imaged.

It can be appreciated that in-vivo analysis systems may be optimized according tot he target selected. Skin tissue analysis, and the monitoring of melanoma, for example, is another application where the inventive system and method can be most useful. Of course, the system and method are also useful outside the realm of biometrics, in such applications as document analysis. The plurality of embodiments cannot each be set forth in detail here; the practitioner is invited to refer to the cited related patents and patent applications for further details about non-invasive systems.

BRIEF DESCRIPTION OF THE DRAWINGS

The following drawings are provided an aid to understanding the invention.

DETAILED DESCRIPTION OF AN EMBODIMENT OF THE INVENTION

Figure 1:
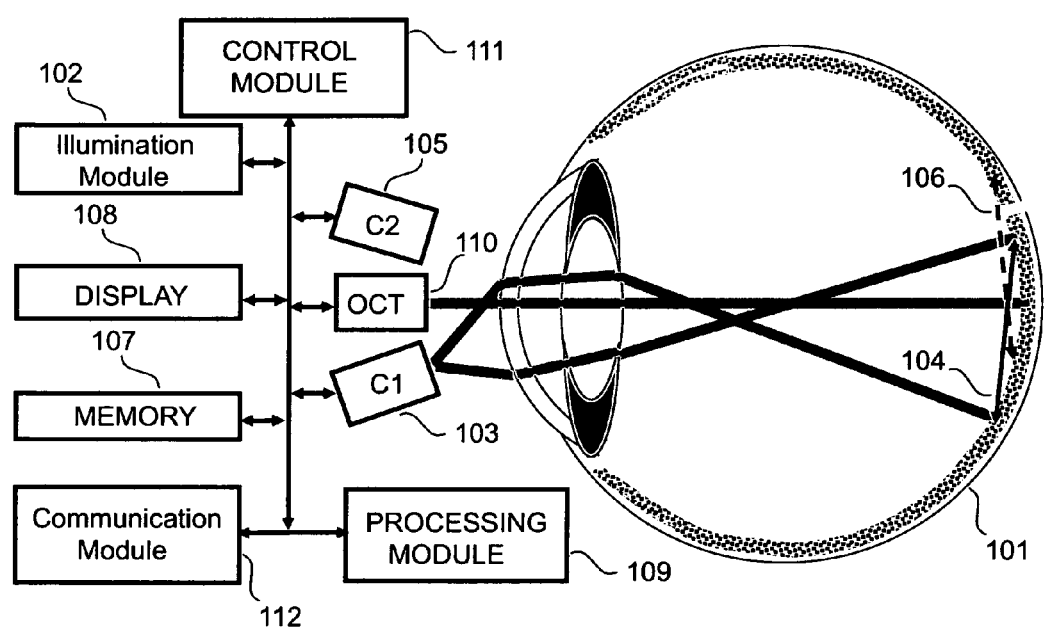
FIG. 1 is a schematic type illustration of a preferred embodiment of the system that includes multiple off-axis cameras and an OCT system.

The invention taught herein includes a device and method of non-invasively analyzing and imaging an eye using optical radiation. The preferred embodiment is described in FIG. 1 and includes a multiplicity of optical radiation sources in an illumination module, a multiplicity of cameras, memory, a display module, a processing module, an OCT system, a control module and a communications module.

In the preferred embodiment the inventive device analyzes an eye 101 (of FIG. 1) by; intermittently illuminating the eye with radiation at or centered about an infra-red wavelength by means of an illumination module 102; synchronously capturing (with respect to the above intermittent radiation) at least some of the infra-red radiation with at least one camera 102 where said captured radiation forms an image. The camera makes the image available to memory 107 and a display 108.

The radiation wavelength or wavelength range is selected to be in a range where the eye has reduced sensitivity and therefore does not cause the iris to close, thus allowing off-axis cameras to capture extensive images of the retina. Referring again to FIG. 1, camera C1 103 could capture an image of the retinal area indicated by double headed solid arrow 104, while a second camera C2 105 could image a retinal area indicated double headed dashed arrow 106.

It can be appreciated that the two imaged retinal areas overlap in the central region. The overlap allows the images to be registered with respect to each other and provides greater detail in the overlapping region, which could be a region of great interest such as the fovea. It can be appreciated that a multiplicity of cameras can be used.

Interleaved with illumination by infra-red radiation is a short burst of radiation at a second selected wavelength which could be in the visible range. As used herein interleaved means that the second radiation is generated during a period when the first radiation is off. This could be done repeatedly at more than two different wavelength. The second image may be combined with the first image in the processing module.

When the second radiation is in the visible range, the short burst should be of sufficiently brief duration to be complete in a time frame that is shorter than the response time of the eye to close the iris. As a consequence the image is obtained more quickly than the iris can close.

The stored acquired images may be processed either by a local processing module 109 or transmitted via the communication module 112 for remote processing. Processing can include but is not limited to: adding images to get enhanced multispectral images; subtracting images, for example, subtracting a red image to remove the predominantly red vascular components of the retina.

Referring again to FIG. 1, the method further includes the additional steps of performing at least one interferometric based depth scan by means of an interferometric device at a first location of at least one component of the eye. In the preferred embodiment the interferometric device is an OCT device. According to the inventive method the location of the depth scan is registered with the first image because the location of interferometric device with respect to one or more cameras.

Having one or more depth scans of the retina at known locations with respect to an image of the retina provides the opportunity to measure and monitor one or more characteristics of the eye that are symptomatic of propensity to, onset of, progression of, or regression of a disease or malignant condition.

An example of such a characteristic is a layer thickness of the retina. In particular a decrease in the thickness of a retinal layer, such as the retinal nerve fiber layer, is a symptom of the onset of glaucoma. Measurements of layer thickness, or of layer separation or of layer protrusion of the retina are also valuable in relation to macular degeneration.

Generating more than one depth scan may be accomplished by movement of the eye or by by means of conventional lateral or angular scanning techniques. Conventional scanning in one dimension provides a two dimensional image of a portion of the eye. Conventional scanning in two dimensions provides an image that has three spatial dimensions.

Generating more than one depth scan may be accomplished by movement of the eye can be accomplished in a controlled manner by manipulating a variable fixation point on a display visible to the test subject (owner of the eye). It can be appreciated that in humans with two eyes a variable fixation point may be presented to either or both eyes since they track. The location of such a variable fixation point may be controlled to manipulate the relative position of a camera with respect to an eye to observe a region of interest in the eye.

Such manipulation of the fixation point may be accomplished by the test subject observing the display, by third party observing the display or by computer controlled means. Registration of the OCT depth scans with respect to one or more cameras will ensure the observer can locate the region of interest and ensure that depth scans are acquired at an appropriate location, for example at the center of the fovea.

Referring again to FIG. 1 an optional communication module enables acquired images, scans and measurements to be transmitted via the Internet or WiFi or other means for remote processing, output or storage.

Figure 2:
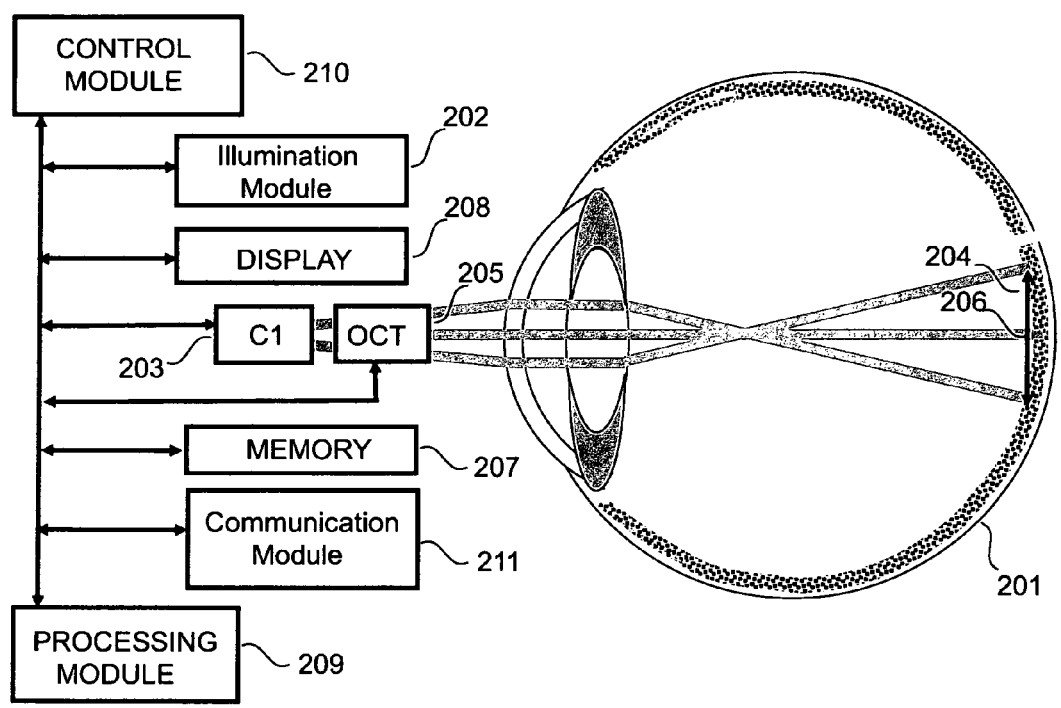
FIG. 2 is a schematic type illustration of an embodiment with a single camera viewing through an OCT system component.

FIG. 2 illustrates an embodiment which in many respects is similar to the preferred embodiment. However in this embodiment a single on-axis camera C1 203 is in line with an OCT system which permits a viewing through to the target. One such OCT system is described in U.S. patent application Ser. No. 12,924,316 (incorporated by reference herein).

This embodiment is useful to a third party viewing a test subject's eye. For optimal results the OCT system 205 will operate at a different wavelength than the camera C1 203. An advantage of this system is that the camera can operate at visible wavelengths with an OCT system operating at an infra-red wavelength range. This is superior to currently used instruments in that it provides one or more OCT depth scans at known locations with respect to an image of the retina.

Figure 3:
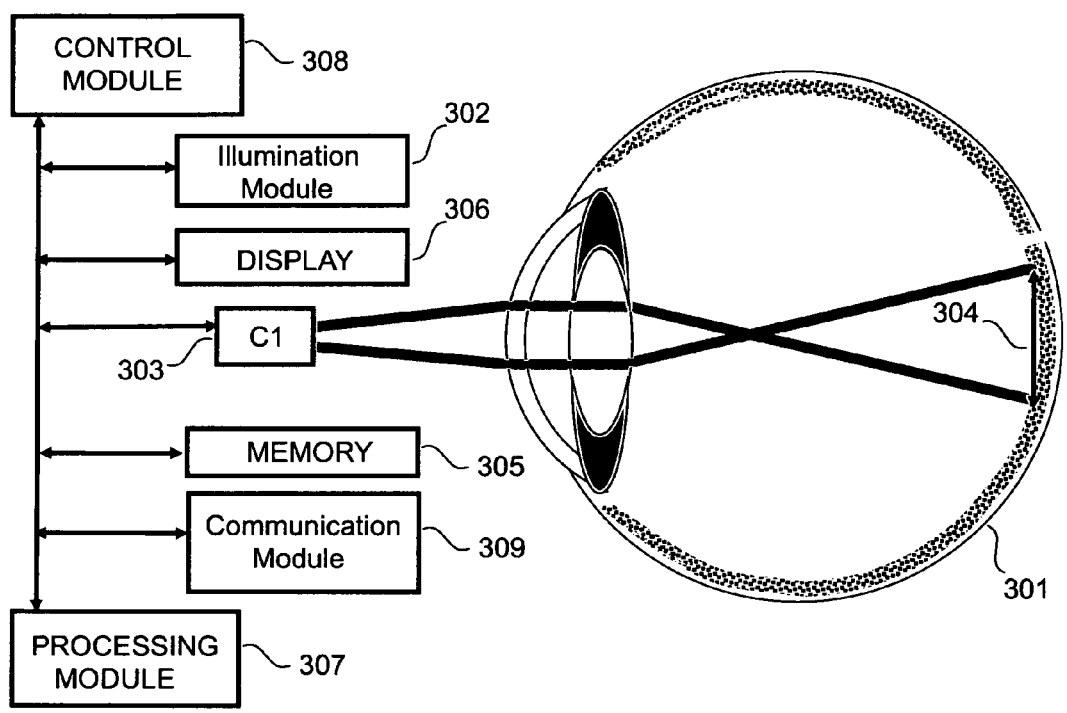
FIG. 3 is a schematic type illustration of an embodiment not including an OCT system.

FIG. 3 illustrates an embodiment which in many respects is similar to the preferred embodiment. However in this embodiment a single on-axis camera C1 303 is used with an illumination module 302 that provides illumination at a multiplicity of wavelengths in both infra-red and visible ranges. This especially useful in generating a processed image exploiting the multi-spectral information.

Figure 4:
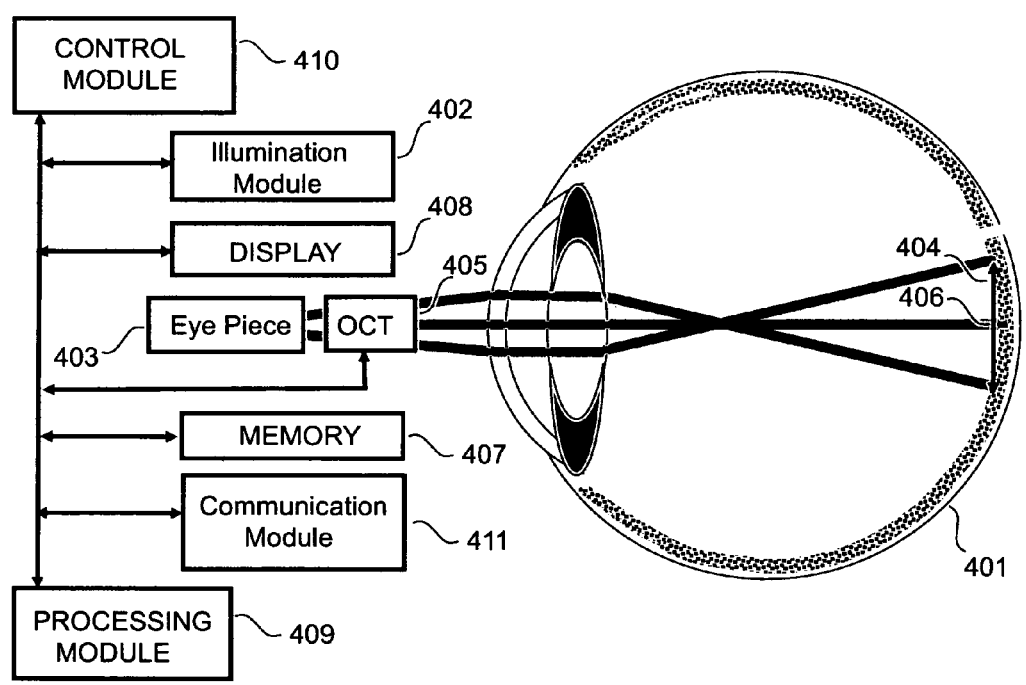
FIG. 4 is a schematic type illustration of an embodiment suitable for third part direct viewing for visual inspection and measurement.

FIG. 4 illustrates an embodiment which in many respects is similar to the preferred embodiment. However in this embodiment an OCT system 405 and an eye-piece 403 for direct viewing of an eye of a test subject by a third party. Similar to FIG. 2 the OCT system permits through viewing especially at visible wavelengths. The eye piece provides an optical path equivalent to a conventional ophthalmoscope.

While a conventional ophthalmoscope simply provides images, this embodiment provides additional critical measurements obtained by the OCT system. For example, it could provide retinal nerve fiber layer thickness data at known locations with respect to the image of the retina. It can be appreciated that an instrument according to this invention could display information such as retinal layer thickness in real time similar in concept to a heads up display.

Figure 5:
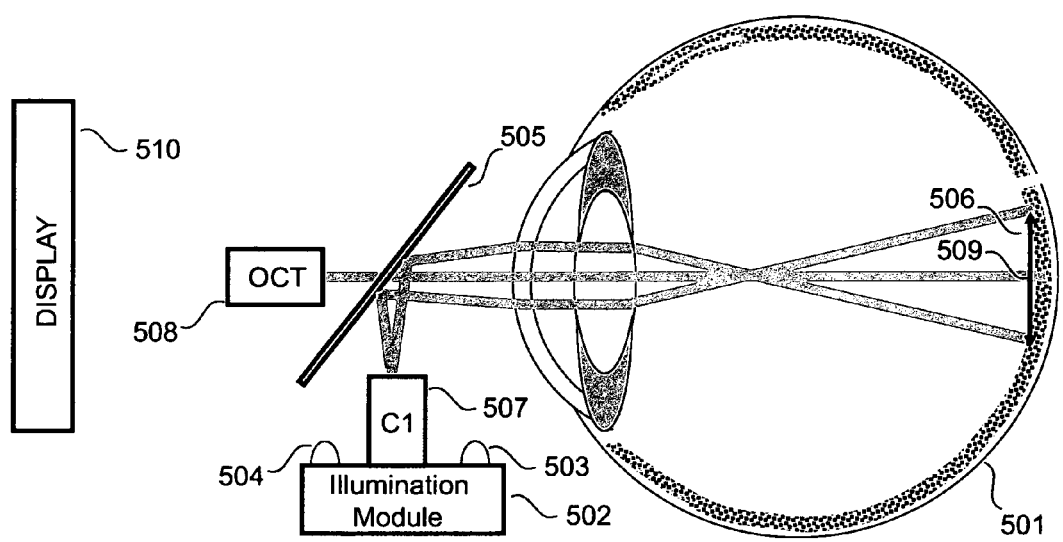
FIG. 5 is a schematic type illustration of a possible configuration of elements of invention.

FIG. 5 is an alternate embodiment showing an illumination module 502 with two LEDs 503 and 504 of ring of LEDs. A mirror surface 505 would reflect at wavelengths of the LEDs while transmitting light at the wavelength of the OCT system 508. In this embodiment a view through OCT system would enable the test subject to view the display with the eye under test.

It can be appreciated that one or more displays could be used. For example one or two displays could be available to the test subject for one or other or both eyes, with additional displays available for local viewing by a third party or remotely either in (quasi) real time or at a later time.

It can also be appreciated that displays, cameras and processing capabilities of consumer devices, including but not limited to, phones, tablets, computers, etc., may be used as components of the system. Furthermore in mobile or home applications the system may be used as an attachment of such consumer devices and exploit the display, camera and processing features.

While the above description has focused mainly on the retina of the eye, this emphasis is to illustrate the usefulness of the invention. It can be appreciated that the invention can also be used to measure or image other aspects of the eye, such as axial length of the eye or other characteristics of the eye such as a layer thickness of a component in the anterior chamber.

The system may exploit other optical components as may be useful according to the application. For example, an adaptive optic in the optical path of the camera such as an adaptive lens allows flexibility in range of focus. Similarly an adaptive optic in the optical path of the interferometric likewise provides flexibility in range of focus.

The invention is also useful for tissues other than eye tissue. For example the combination of multi-spectral imaging and OCT depth scanning is useful for inspecting skin tissue for malignancies, such as melanoma.

The invention is not limited to biological applications. For example the combination of multi-spectral imaging and OCT depth scanning is useful for document authentication, such as currency authentication or art authentication.

Other examples will be apparent to persons skilled in the art. The scope of this invention should be determined with reference to the specification, the drawings and the appended claims, along with the full scope of equivalents as applied thereto.

What is claimed is:

1. A method of non-invasively analyzing an eye wherein said method includes the steps of:
   intermittently illuminating said eye with first radiation at at least one first wavelength;
   synchronously capturing at least some of said first radiation with at least one camera to form a first image;
   storing said first image in memory;
   displaying said first image on at least one viewing device;
   observing said displayed first image;
   manipulating the relative position of said camera with respect to said eye to observe a region of interest in the eye; and
   storing at least one of said displayed images.

2. The method of claim 1, wherein the step of illuminating said eye further includes selecting said first radiation such that said eye has reduced sensitivity to said first radiation.

3. The method of claim 1, wherein said step of illuminating said eye with said first radiation includes the step of selecting said first radiation as infra-red radiation.

4. The method of claim 1, wherein said step of intermittently illuminating said eye with said first radiation, is interleaved with the further step of: illuminating said eye with at least one short burst of a second radiation at a second wavelength; synchronously capturing at least a portion of said second radiation with at least one camera to form a second image; storing said second image in memory; and combining said second image with said first image.

5. The method of claim 4, wherein the step of illuminating said eye with at least one short burst further includes selecting the duration of said short burst to be sufficiently short to be complete in a time frame that is shorter than the response time of the eye.

6. The method of claim 1, wherein additionally said step of synchronously capturing at least some of said first radiation with at least one camera to form a first image is combined with the step of synchronously capturing at least some of said first radiation with at least one additional second camera to form a second image that overlaps with said first image.

7. The method of claim 1, with the additional steps of performing at least one interferometric based depth scan by means of an interferometric device at a first location of at least one component of the eye wherein the location of said depth scan is registered with said first image.

8. The method of claim 7, wherein the location of said depth scan is registered with said first image by the relative location of said first or second camera with respect to said interferometric device.

9. The method of claim 8, with the additional steps of processing said depth scan to measure a characteristic of said eye at a known location with respect to said first image or second image.

10. The method of claim 1, wherein the step of manipulating the relative position of said camera with respect to said eye to observe a region of interest in the eye is accomplished by means of a variable fixation point.

11. A system for non-invasively analyzing a target wherein said system comprises:
   an illumination module operable to intermittently illuminate said target with first radiation at at least one first wavelength, a camera operable to synchronously capture at least some of said first radiation to form a first image, a memory operable to store said first image, a display operable to display said first image on at least one viewing device, a control module operable to manipulate the relative position of said camera with respect to said target to observe a region of interest in said target, an OCT system operable to perform at least one interferometric based depth scan by means of an interferometric device at a first location of at least one component of said target, wherein the location of said depth scan is registered with said first image obtained by said first camera.

12. A system as in claim 11, wherein said illumination module performs so as to intermittently illuminate said eye with said first radiation, and said intermittent illumination of said eye at said first radiation is interleaved with illuminating said eye with at least one short burst of a second radiation at a second wavelength; and synchronously capturing at least a portion of said second radiation with at least one camera to form a second image; storing said second image in memory; and combining said second image with said first image.

13. A system as in claim 11 further including at least one second camera, said second camera synchronously capturing at least some of said second radiation, to form a second image, and where said first image from said first camera and said second image from said second camera overlap.

14. The system of claim 12, wherein said illumination module performs so as to illuminate said eye with at least one short burst, and the duration of said short burst is sufficiently short so that said burst is complete in a time frame that is shorter than the response time of the eye.

15. The system of claim 11, where said OCT system performs at least one interferometric based depth scan by means of an interferometric device at a first location of at least one component of the eye wherein the location of said depth scan is registered with said first image.

16. The system of claim 15 wherein the location of said depth scan is registered with said first image by the relative location of said first camera with respect to said interferometric device.

17. The system of claim 16 wherein said system further includes at least one processing module, said processing module processing said depth scan to measure a characteristic of said eye at a known location with respect to said first image or second image.

* * * * *